United States Patent
Awais et al.

(10) Patent No.: US 11,590,004 B2
(45) Date of Patent: Feb. 28, 2023

(54) FEMORAL HEAD CENTRE OF ROTATION LOCATING DEVICE

(71) Applicant: DEPUY IRELAND UNLIMITED COMPANY, County Cork (IE)

(72) Inventors: Arda Awais, Chigwell (GB); Eleanor Donald Fathers, Tottenham (GB); Caroline Fletcher, Birmingham (GB); Chierol Lai, Rotterdam (NL)

(73) Assignee: DEPUY IRELAND UNLIMITED COMPANY

( * ) Notice: Subject to any disclaimer, the term of this patent is extended or adjusted under 35 U.S.C. 154(b) by 499 days.

(21) Appl. No.: 16/618,851

(22) PCT Filed: Jun. 1, 2018

(86) PCT No.: PCT/EP2018/064415
§ 371 (c)(1),
(2) Date: Dec. 3, 2019

(87) PCT Pub. No.: WO2018/224399
PCT Pub. Date: Dec. 13, 2018

(65) Prior Publication Data
US 2021/0128321 A1    May 6, 2021

(30) Foreign Application Priority Data
Jun. 9, 2017 (GB) .................................. 1709210

(51) Int. Cl.
*A61F 2/46* (2006.01)
*A61B 17/17* (2006.01)
*A61F 2/36* (2006.01)

(52) U.S. Cl.
CPC .......... *A61F 2/4657* (2013.01); *A61B 17/175* (2013.01); *A61F 2/3609* (2013.01);
(Continued)

(58) Field of Classification Search
CPC ................. A61B 17/175; A61F 2/4657; A61F 2002/4658
See application file for complete search history.

(56) References Cited

U.S. PATENT DOCUMENTS 4,896,663 A * 1/1990 Vandewalls .......... A61B 17/175
606/85
5,520,694 A 5/1996 Dance et al.
(Continued)

FOREIGN PATENT DOCUMENTS

DE    69418040 E    12/1999
DE    69424416 E    1/2001
EP     0705075 A1    4/1996

OTHER PUBLICATIONS

EP International Search report for PCT/EP2018/064415 dated Sep. 4, 2018.
(Continued)

*Primary Examiner* — Nicholas W Woodall

(57) ABSTRACT

The invention provides a femoral head centre of rotation locating device (10) comprising an adjustable frame (12) having a frame axis (X). The frame includes a central frame portion (14); a first jaw (16) that is linearly moveable relative to the central frame portion along the frame axis and having a first femoral head contacting surface (26); a second jaw (18) that is linearly moveable relative to the central frame portion along the frame axis and having a second femoral head contacting surface (28), and a gear wheel (32) mounted on the central frame portion. The gear wheel has a
(Continued)

centric aperture (34) located substantially equidistant from the first and second femoral head contacting surfaces. The gear wheel is operably connected to each of the first and second moveable jaws by gear teeth (30) provided on a surface of each of the first and second moveable jaws. Linear movement of the first jaw in a first direction rotates the gear wheel to cause reciprocal linear movement of the second jaw to maintain the centric aperture at a position equidistant from the first and second femoral head contacting surfaces. This aligns the centric aperture with the native head centre of the femur as the first and second femoral head contacting surfaces come into contact with opposite surfaces of the femoral head.

10 Claims, 12 Drawing Sheets

(52) U.S. Cl.
CPC ..... *A61F 2/4607* (2013.01); *A61F 2002/3611* (2013.01); *A61F 2002/3625* (2013.01); *A61F 2002/4658* (2013.01)

(56) References Cited

U.S. PATENT DOCUMENTS

| | | | |
|---|---|---|---|
| 5,611,353 | A | 3/1997 | Dance et al. |
| 6,258,097 | B1* | 7/2001 | Cook ................ A61F 2/4657 606/91 |
| 2005/0113841 | A1* | 5/2005 | Sheldon ............ A61B 17/1668 606/88 |
| 2009/0076507 | A1 | 3/2009 | Claypool et al. |
| 2010/0137924 | A1* | 6/2010 | Tuke ................ A61B 17/175 606/86 R |
| 2010/0292743 | A1* | 11/2010 | Singhal ............ A61B 17/175 606/86 R |
| 2011/0077650 | A1* | 3/2011 | Braun ............... A61B 17/175 606/56 |
| 2014/0276866 | A1 | 9/2014 | Endsley et al. |

OTHER PUBLICATIONS

GB Search Report under Section 17 for GB 1709210.7 dated Nov. 29, 2017.

* cited by examiner

FEMORAL HEAD CENTRE OF ROTATION LOCATING DEVICE

CROSS REFERENCE TO RELATED APPLICATION

This application is a National Stage Application filed Under 35 U.S.C. § 371 of International Application No. PCT/EP2018/064415 filed Jun. 1, 2018, published Dec. 13, 2018 as International Publication No. WO2018/224399, which claims priority to GB1709210.7 filed Jun. 9, 2017, now abandoned, entitled "Femoral Head Centre of Rotation Locating Device" which is hereby incorporated by reference in its entirely.

FIELD OF THE INVENTION

This invention relates to the field of orthopaedics, and more particularly to devices and methods for locating an anatomic centre of a native femoral head.

BACKGROUND TO THE INVENTION

A femur includes a femoral head which has a femoral head centre. During an orthopaedic surgical procedure a surgeon may need to identify the femoral head centre to facilitate alignment of surgical instruments and positioning of orthopaedic implants.

Leg length discrepancy is a common issue following total hip replacement. In the UK, the NHS performed 65,648 hip replacements in 2016. Of these, 10-16% of patients suffer from post-operative leg length discrepancy. Current clinical methods of restoring the anatomical leg length, which aim to re-establish the native head centre of a femur with an implanted prosthesis, often rely on the surgeon measuring a set of distances on the native femoral head and undertaking calculations to determine the femoral head centre. Such methods are time consuming and can be error prone, particularly as the surgeon is having to undertake calculations under time pressure.

During a medical procedure, the native head of the femur is often resected early in the procedure, which makes it difficult to position a head centre of the final prosthesis at the same location and orientation as the native head centre of the femur.

There is a need for a device that provides the surgeon with a quick and reliable determination of the femoral head centre. There is also a need for a device which enables the surgeon to ensure that the trial femoral head, and hence the final implant has a centre of rotation that matches that of the native femur. This will result in a reduced likelihood of leg length discrepancy.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to a first aspect of the invention there is provided a femoral head centre of rotation locating device comprising:
 an adjustable frame having a frame axis, the frame comprising:
  a central frame portion;
  a first jaw that is linearly moveable relative to the central frame portion along the frame axis and having a first femoral head contacting surface;
  a second jaw that is linearly moveable relative to the central frame portion along the frame axis and having a second femoral head contacting surface, and
  a gearwheel mounted on the central frame portion, the gear wheel having a centric aperture located substantially equidistant from the first and second femoral head contacting surfaces, the gear wheel being operably connected to each of the first and second moveable jaws by gear teeth provided on a surface of each of the first and second moveable jaws,
 wherein linear movement of the first jaw in a first direction rotates the gear wheel to cause reciprocal linear movement of the second jaw to maintain the centric aperture at a position equidistant from the first and second femoral head contacting surfaces to align the centric aperture with the native head centre of the femur as the first and second femoral head contacting surfaces come into contact with opposite surfaces of the femoral head.

In some constructions of the device, each of the first and second jaws includes an end wall and a pair of arms extending therefrom. Gear teeth may be provided at least partially along an inner surface of one of the pair of arms of the first jaw. Similarly, gear teeth may be provided at least partially along an inner surface of one of the pair of arms of the second jaw.

In some constructions of the device, the central frame portion includes a first channel dimensioned to receive one of the pair of arms of the first jaw and one of the pair of arms of the second jaw, in a sliding relationship. The central frame portion also includes a second channel dimensioned to receive one of the pair of arms of the first jaw and one of the pair of arms of the second jaw in a sliding relationship.

In some constructions of the device, each of the first femoral head contacting surface and the second femoral head contacting surface comprises a projection extending from the end wall of each of the first and second jaws. In some constructions, the projection comprises a pair of spaced apart posts. The device is positioned to span the widest point of the femoral head. The jaws can be moved towards each other or moved away from each other until the first femoral head contacting surface and the second femoral head contacting surface make contact with the surface of the femoral head.

Advantageously, the sliding relationship between the opposing jaws of the device enables a surgeon to manipulate the device into place on the femoral head using one hand. This leaves the other hand free to carry out other activities, such as marking the centre of rotation of the femoral head.

The centric aperture of the gear wheel may be dimensioned to receive a bone marking element for marking the position of the femoral head centre of rotation onto the femoral head. The bone marking element may include a first end configured to pierce the bone (e.g., a spiked portion) and second end configured to be impacted. A bone marking element may be provided with the device, already positioned within the centric aperture. Alternatively, the surgeon may insert a bone marking element.

In addition to providing the aforementioned device which enables a surgeon to simply and reliably establish the centre of rotation of a native femoral head, advantageously, a kit is also provided which enables the surgeon to additionally ensure that a selected trial femoral head component re-establishes this determined centre of rotation of the native femoral head.

Accordingly, according to a second aspect of the invention there is provided a kit for use in comparing the position of a femoral head centre of rotation of a native femoral head and a trial femoral head component, the kit comprising:

(a) an adjustable frame having a frame axis, the frame comprising:
   a central frame portion;
   a first jaw that is linearly moveable relative to the central frame portion along the frame axis and having a first femoral head contacting surface;
   a second jaw that is linearly moveable relative to the central frame portion along the frame axis and having a second femoral head contacting surface, and
   a gearwheel mounted on the central frame portion, the gear wheel having a centric aperture located substantially equidistant the first and second femoral head contacting surfaces, the gear wheel being operably connected to each of the first and second moveable jaws by gear teeth provided on a surface of each of the first and second moveable jaws,
wherein linear movement of the first jaw in a first direction rotates the gear wheel to cause reciprocal linear movement of the second jaw to maintain the centric aperture at a position equidistant the first and second femoral head contacting surfaces to align the centric aperture with the native head centre of the femur as the first and second femoral head contacting surfaces come into contact with opposite surfaces of the femoral head.

(b) a trochanter marking device comprising:
   a connection element configured for connecting the trochanter marking device to (i) the femoral head centre of rotation of the native femoral head and (ii) a femoral head centre of rotation of a trial femoral head component, such that the trochanter marking device can pivot about each femoral head centre of rotation, and
   a marking aperture dimensioned for receiving a marking tool for marking the position of the marking aperture on the trochanter.

In some constructions, the trochanter marking device includes a plurality of sections, each section including at least one marking aperture. Adjacent sections may be connected via a frangible connection. This enables the trochanter marking device to be shortened by removal of a section. This is advantageous, as it prevents the device from snagging on soft tissue at the surgical site, which could cause potential damage to the tissue.

Optionally, the marking aperture of the trochanter marking device is dimensioned to receive a cauteriser. However, it is envisaged that other marking tools could be utilised.

In some constructions of the kit, the femoral head centre of rotation locating device and/or the trochanter marking device is made of a plastic. The femoral head centre of rotation locating device and/or the trochanter marking device may be disposable.

According to a third aspect of the invention, there is provided a method of locating a femoral head centre of rotation of a native femur head, the method comprising the steps of:

(i) using a femoral head centre of rotation locating device comprising: an adjustable frame having a frame axis, the frame comprising:
   a central frame portion;
   a first jaw that is linearly moveable relative to the central frame portion along the frame axis and having a first femoral head contacting surface;
   a second jaw that is linearly moveable relative to the central frame portion along the frame axis and having a second femoral head contacting surface, and
   a gearwheel mounted on the central frame portion, the gear wheel having a centric aperture located substantially equidistant the first and second femoral head contacting surfaces, the gear wheel being operably connected to each of the first and second moveable jaws by gear teeth provided on a surface of each of the first and second moveable jaws,
   wherein linear movement of the first jaw in a first direction rotates the gear wheel to cause reciprocal linear movement of the second jaw to maintain the centric aperture at a position equidistant the first and second femoral head contacting surfaces to align the centric aperture with the native head centre of the femur as the first and second femoral head contacting surfaces come into contact with opposite surfaces of the femoral head.
(ii) positioning the first and second femoral head contacting surfaces against contact points of the femoral head that equate to a widest part of the femoral head to align the centric aperture of the gear wheel with the centre of rotation of the native femoral head.

Optionally, the method further comprises the step of marking the position of the centric aperture of the gear wheel on the bone. This step may involve impacting a bone marking element located within the centric aperture of the gear wheel into the bone. The bone marking element may include a first end configured to pierce the bone and second end configured to be impacted.

According to a fourth aspect of the invention, there is also provided a method of comparing a femoral head centre of rotation of a native femoral head with a femoral head centre of rotation of a trial femoral head component, the method comprising the steps of:

(i) locating a femoral head centre of rotation of a native femoral head using the method of the third aspect of the invention;
(ii) connecting a connection element of a trochanter marking device to the femoral head centre of rotation of the native femoral head located in step (i), the trochanter marking device comprising:
   a connection element configured for connecting the trochanter marking device to the femoral head centre of rotation of the native femoral head, and
   a marking aperture dimensioned for receiving a marking tool for marking the position of the aperture on the trochanter at the femoral head centre of rotation of the native femoral head;
(iii) marking at least two positions on the trochanter by pivoting the trochanter marking device to a first position on the trochanter, inserting a marking tool through the marking aperture and marking the trochanter at a first position, and then pivoting the trochanter marking device to a second position on the trochanter, inserting a marking tool through the marking aperture and marking the trochanter at a second position;
(iv) resecting the femoral head to leave a prepared femoral neck;

(v) using a rasp or broach to prepare a cavity in the prepared femoral neck for receipt of a femoral component;
(vi) implanting a femoral component;
(vii) assembling a trial femoral head component onto the implanted femoral component;
(viii) connecting a connection element of the trochanter marking device to the femoral head centre of rotation of the trial femoral head component;
(ix) pivoting the trochanter marking device to the first and second marks made on the trochanter made in step (iii);
(x) assessing whether the marking aperture used to mark the first and second marks overlies each of the first and second marks.

In some constructions, the femoral component in step (vi) of the above method is a construct of a broach or a rasp with a trial femoral neck component. In other constructions, the femoral component in step (vi) is a femoral stem component.

In some constructions, the connection element of the trochanter marking device is received within an aperture (e.g., a slot) located at the centre of rotation of the trial femoral head.

BRIEF DESCRIPTION OF THE INVENTION

Constructions of the femoral head centre of rotation locating device will be described hereinafter, by way of example only, with reference to the accompanying drawings in which like reference signs relate to like elements and in which.

DETAILED DESCRIPTION

Constructions of the femoral head centre of rotation locating device are described in the following with reference to the accompanying drawings.

Figure 1:
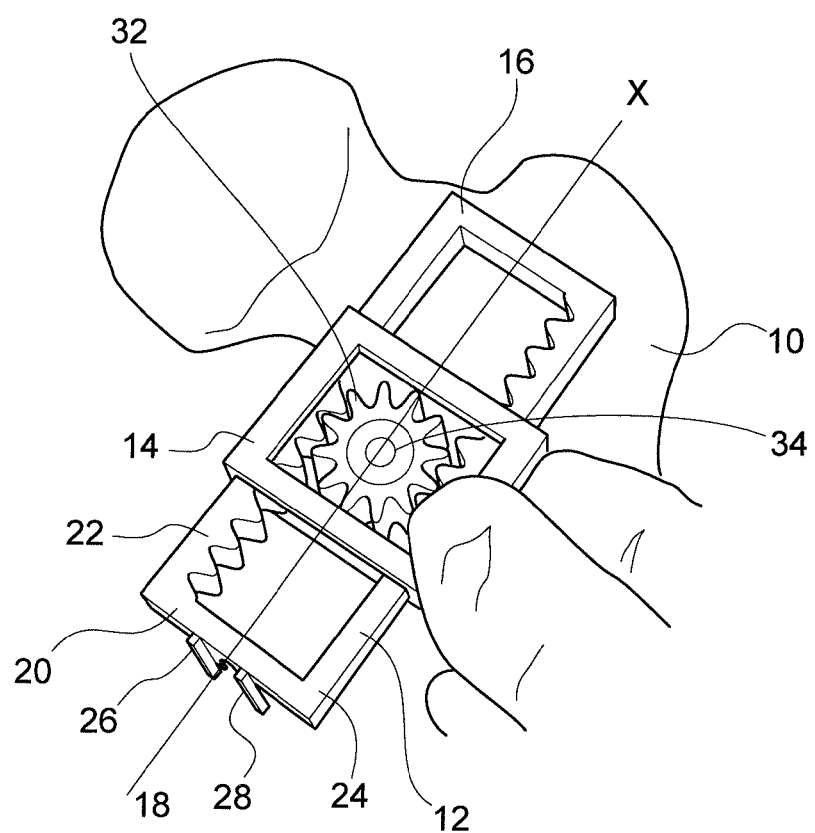
FIG. 1 is a top view of an embodiment of a femoral head centre of rotation locating device according to the invention.
Figure 2:
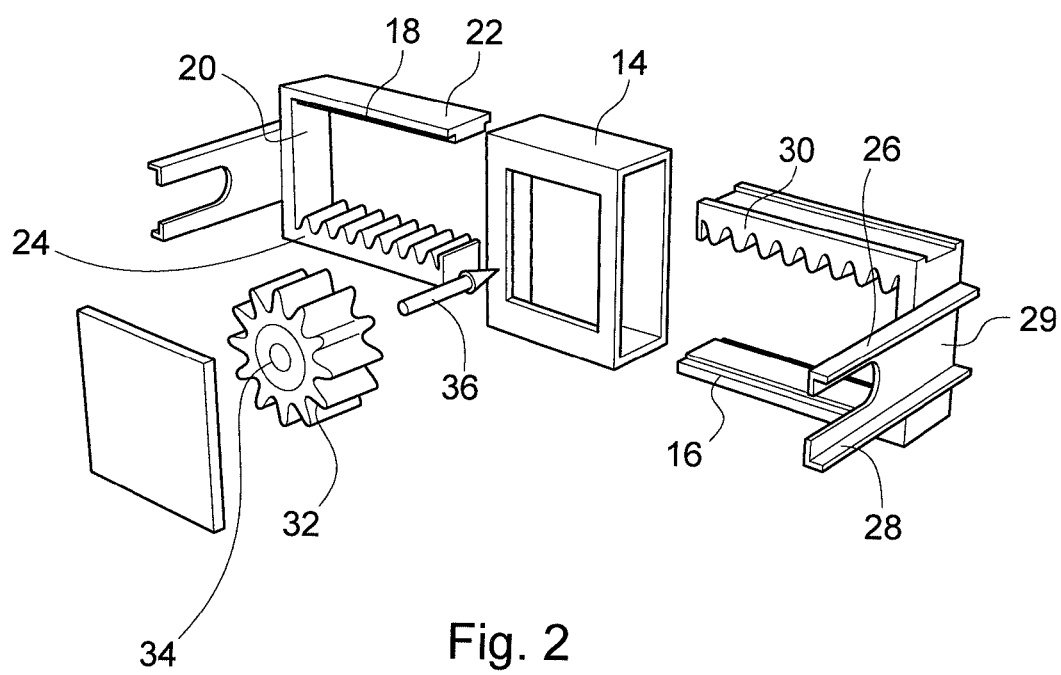
FIG. 2 is an exploded view of the device shown in FIG. 1.

FIGS. 1 and 2 show a first embodiment of a femoral head centre of rotation locating device 10. The device includes an adjustable frame 12 with a frame axis X. The adjustable frame includes a central frame portion 14, a first jaw 16 that is linearly moveable relative to the central frame portion along the frame axis X and a second jaw 18 that is also linearly moveable relative to the central frame portion along the frame axis X.

Each of the first and second jaws 16, 18 has an end wall 20 and two arms 22, 24 extending perpendicularly from the end wall.

The end wall of each jaw is provided with a femoral head contacting surface 26, 28, respectively. In this embodiment, each femoral head contacting surface 26, 28 includes two spaced apart posts joined by a brace portion 29. The free, lower edge of the brace portion has a curved profile. This curved profile is ergonomically designed for the surgeon's fingers to fit through and feel the bone of the femoral head.

One of the arms 24 of each of the first and second jaws includes a plurality of gear teeth 30 extending inwardly. The gear teeth 30 interact with a gearwheel 32 mounted on the central frame portion. The gearwheel has a centric aperture 34 that is located substantially equidistant from the first and second femoral head contacting surfaces 26, 28.

Linear movement of the first jaw in a first direction rotates the gear wheel to cause reciprocal linear movement of the second jaw to maintain the centric aperture at a position equidistant from the first and second femoral head contacting surfaces. This aligns the centric aperture 34 with the native head centre of the femur as the first and second femoral head contacting surfaces come into contact with opposite surfaces of the femoral head.

Figure 3A:
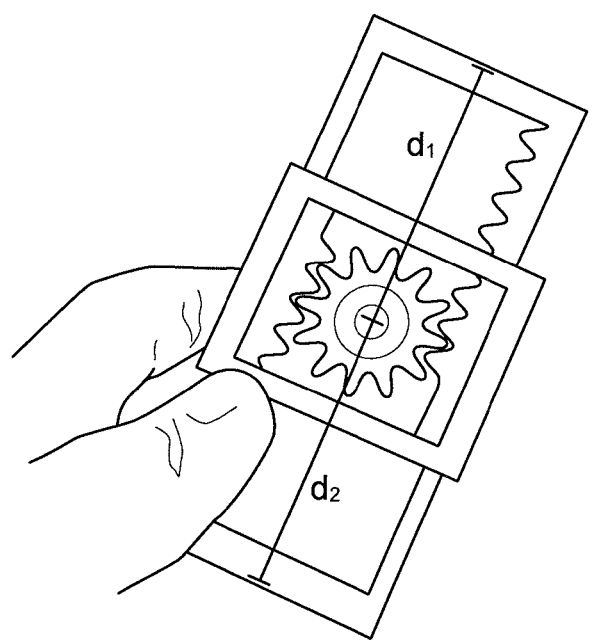
FIG. 3 shows the device prior to use (FIG. 3a) and located on a femoral head (FIG. 3b)

As shown in FIG. 3a, the distance between the centric aperture 34 and the femoral head contacting surface (i.e., the posts) on the first jaw 16 is $d_1$. The distance between the centric aperture 34 and the femoral head contacting surface (i.e., the posts) on the second jaw 18 is $d_2$, with $d_2$ being the same as $d_1$.

During use, the surgeon brings the femoral head contacting surface on the first and second jaws 26, 28 into contact with the femoral head at its widest point. To do this, the jaws are moved linearly towards or away from each other. This causes the gearwheel to rotate either clockwise or anti-clockwise.

Figure 3B:
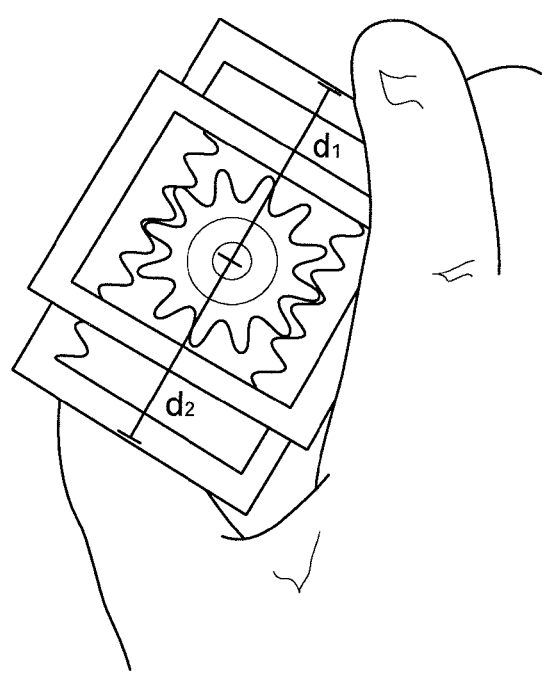

As can be seen from FIG. 3b, the distance $d_1$ is reduced. This causes the gearwheel 32 to rotate clockwise. This draws the second jaw towards the first jaw, such that the distance $d_2$ is reduced the same amount that the distance $d_1$ was reduced. This reciprocal linear movement of the first and second jaw ensures that the centric aperture 34 is maintained at a position equidistant the first and second femoral head contacting surfaces.

The centric aperture includes a removable bone marking element 36. This can be provided within the centric aperture, or provided as a separate component and inserted into the centric aperture by the surgeon. The bone marking element 36 includes a first end configured (e.g., a spike) to pierce the bone and second end configured to be impacted.

Figure 4:
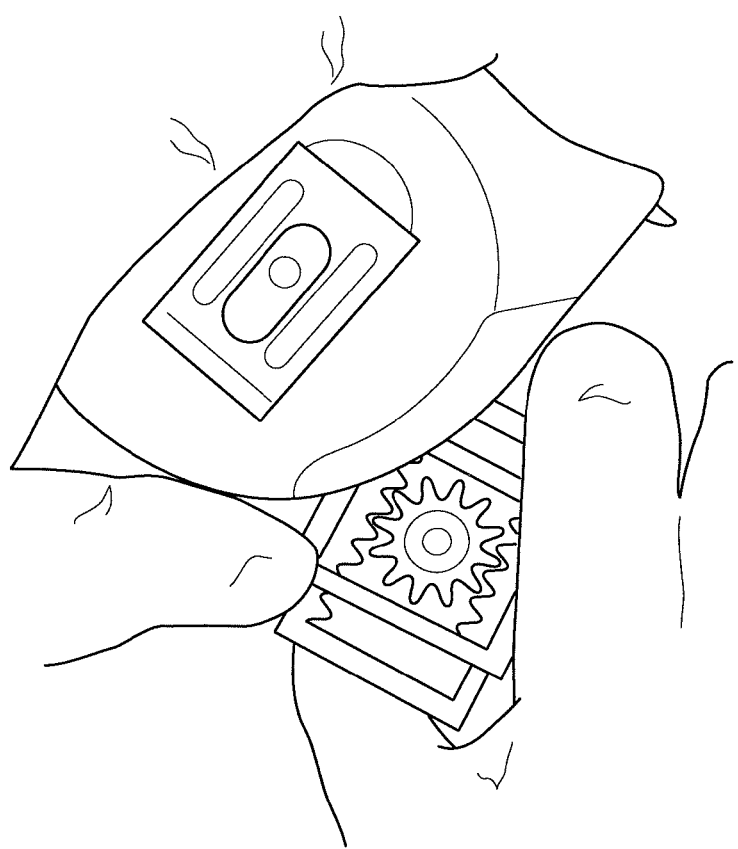
FIG. 4 shows how the device is used to mark the femoral head centre.

Once the centric aperture 34 of the gearwheel 32 has been aligned with the centre of rotation of the native femoral head, the user can impact the bone marking element 36 using, for example, a hammer. This is shown in FIG. 4. The impaction results in the first end of the bone marking element 36 piercing the bone. The pierced site acts as a reference mark on the bone to indicate to the surgeon the centre of rotation of the native femoral head.

The femoral head centre of rotation locating device is then removed from the femoral head. In some constructions, particularly those in which the device is made of a plastic, the device may be disposed of.

Figure 5:
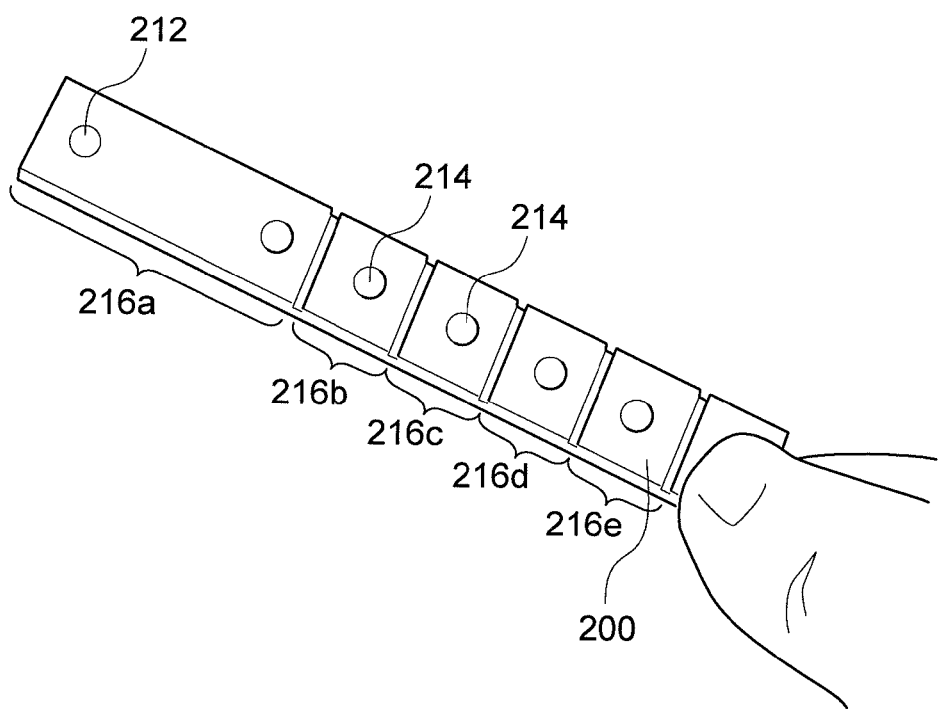
FIG. 5 shows an embodiment of a trochanter marking device according to the invention.
Figure 6:
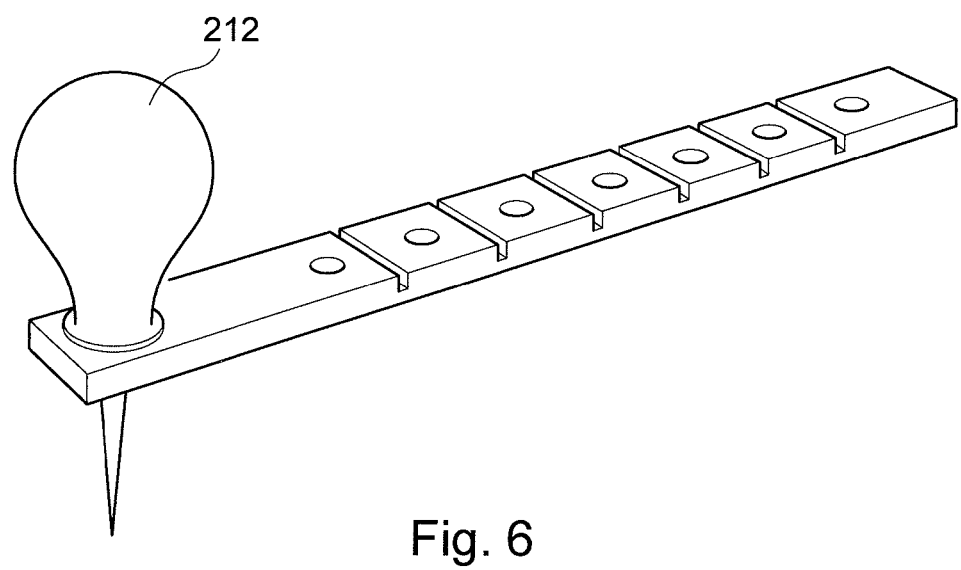
FIG. 6 shows an example of a connection element for connecting the trochanter marking device to the centre of rotation of a femoral head.

In order for a surgeon to assess whether the centre of rotation of a trial femoral head matches the centre of rotation of the native femoral head, the surgeon may utilize a trochanter marking device 200. This device is shown in FIG. 5. The device includes a connection element 212 configured for connecting the trochanter marking device to both (i) the femoral head centre of rotation of the native femoral head and (ii) a femoral head centre of a trial femoral head. The connection element enables the trochanter marking device to pivot about each femoral head centre of the native femoral head and the trial femoral head. The connection element may be a post extending perpendicular to the surface of the device. The connection element may in the form of a pin. A suitable design of pin is shown in FIG. 6. The pin may have a head that is ergonomically designed to feel comfortable between the surgeon's fingers. As shown, the pin head may have a substantially bulbous shape.

The trochanter marking device also includes a marking aperture 214 dimensioned for receiving a marking tool for marking the position of the aperture on the trochanter. The marking tool may be a cauteriser.

Figure 7:
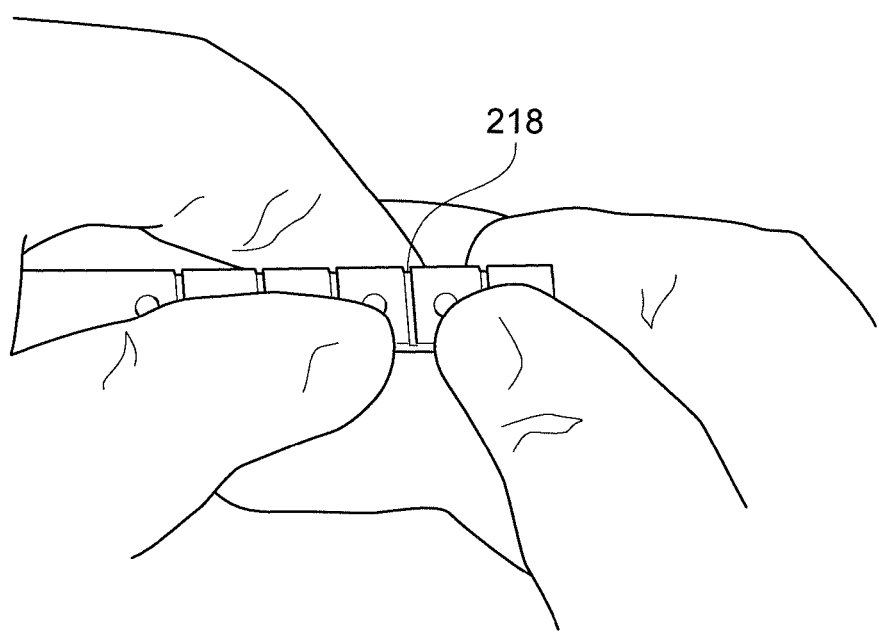
FIG. 7 shows how a user can adapt the length of trochanter marking device to a particular patient by snapping-off a segment of the device.

In some constructions, the trochanter marking device includes a plurality of sections 216a, 216b, 216. Each section includes at least one marking aperture 214. As shown in FIG. 7, adjacent sections may be connected via a breakable connection 218. The breakable connections enable the trochanter marking device to be shortened by removal of one or more sections. This prevents the trochanter marking device from catching on and damaging any soft tissue at the surgical site.

FIGS. 8 to 12 demonstrate pictorially the steps in using the trochanter marking device 200 to determine whether the femoral head centre of rotation has been re-established when a trial femoral head is inserted into the femur.

Figure 8:
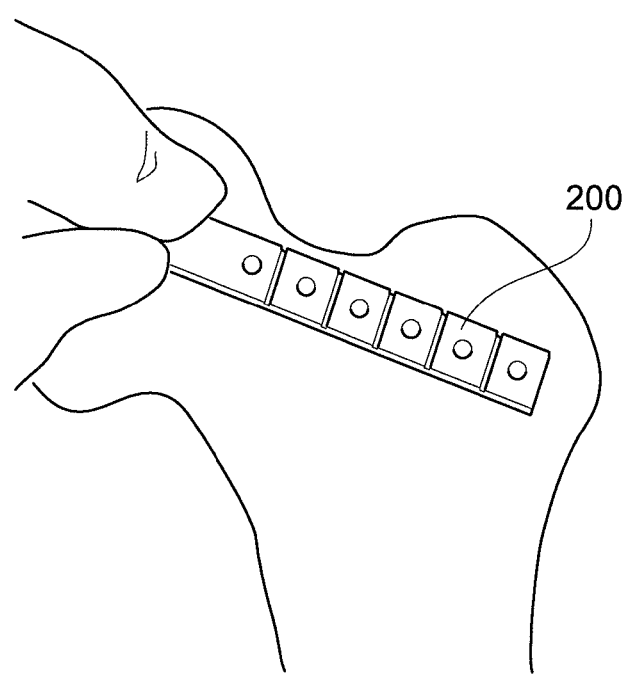
FIG. 8 shows the adapted trochanter marking device of FIG. 7 placed on the trochanter.
Figure 9A:
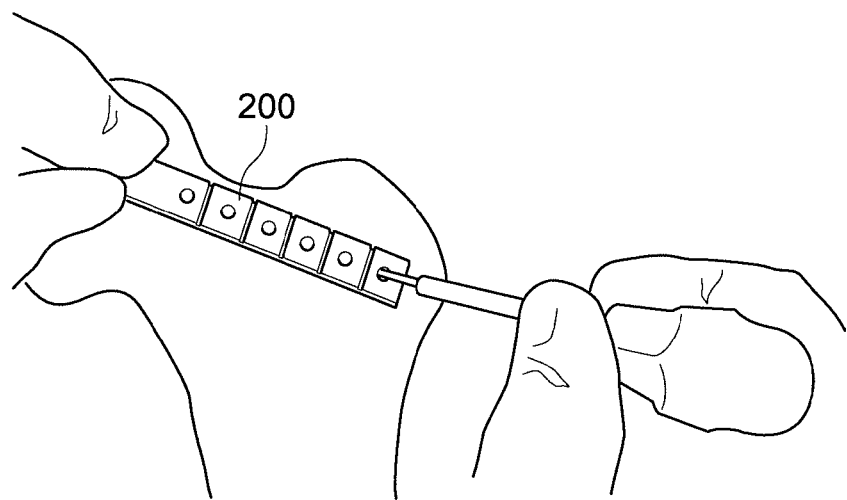
FIG. 9 shows the trochanter marking device being used to make a first mark (FIG. 9a) and second mark (FIG. 9b) on the trochanter.
Figure 9B:
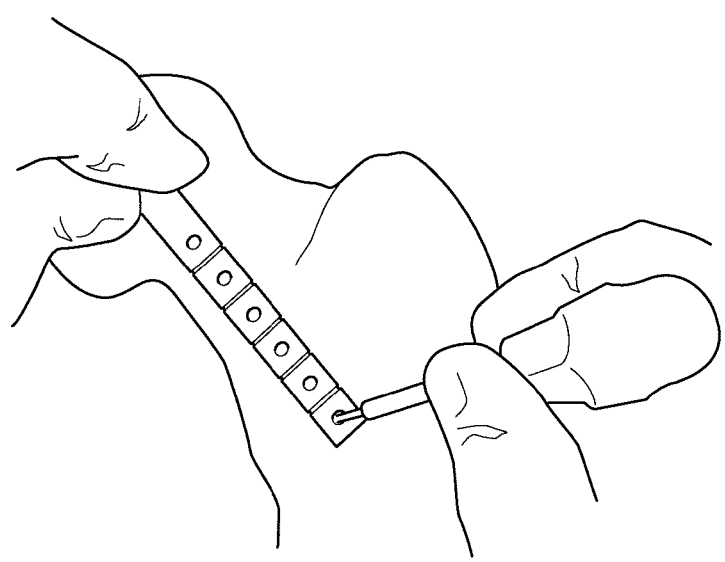

FIG. 8 shows that the connection element of the trochanter marking device 200 is inserted into the reference mark left on the native femoral head by the bone marking element 36. As shown in FIG. 9a, the trochanter marking device 200 is pivoted horizontally to a first position on the trochanter. A bone marking tool (e.g., a cauteriser) is inserted through the marking aperture 214, to mark a first reference position on the bone. As shown in FIG. 9b, the trochanter marking device 200 is then pivoted diagonally to a second position on the trochanter. The bone marking tool (e.g., a cauteriser) is again inserted through the same marking aperture 214, and a second reference mark is made on the bone.

Figure 10:
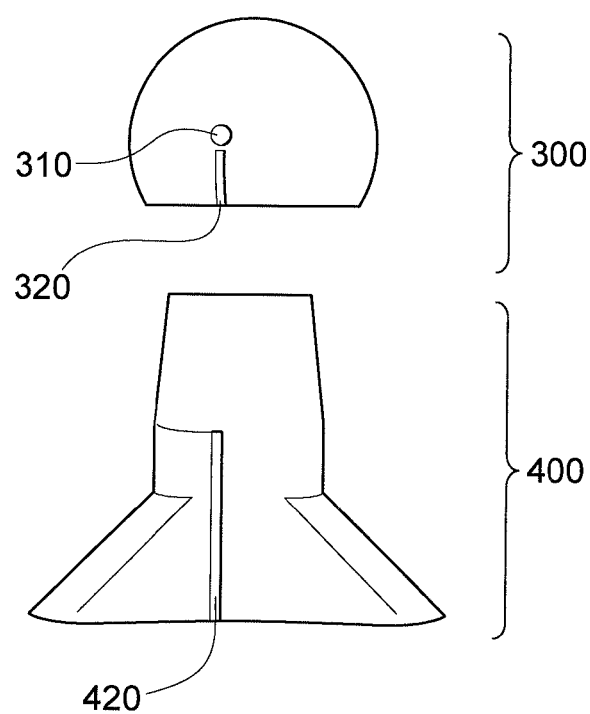
FIG. 10 shows a trial femoral head positioned in the resected femoral neck.

After resection of the femoral neck, a trial femoral head component 300 is inserted into a trial femoral neck component 400. Exemplary trial femoral head and neck components are shown in FIG. 10. The trial femoral head component includes a slot 310 located at the centre of rotation. This slot is dimensioned to receive the connection element of the trochanter marking device 200. The trial femoral head component includes an orientation marker, here shown as a vertically orientated groove 320. The trial femoral neck component 400 also includes an orientation marker, here shown as a vertically orientated groove 420. Alignment of the groove 320 on the trial femoral head component 300 with the corresponding groove 420 on the trial femoral neck component 400 ensures correct orientation of the trial femoral head component.

Figure 11:
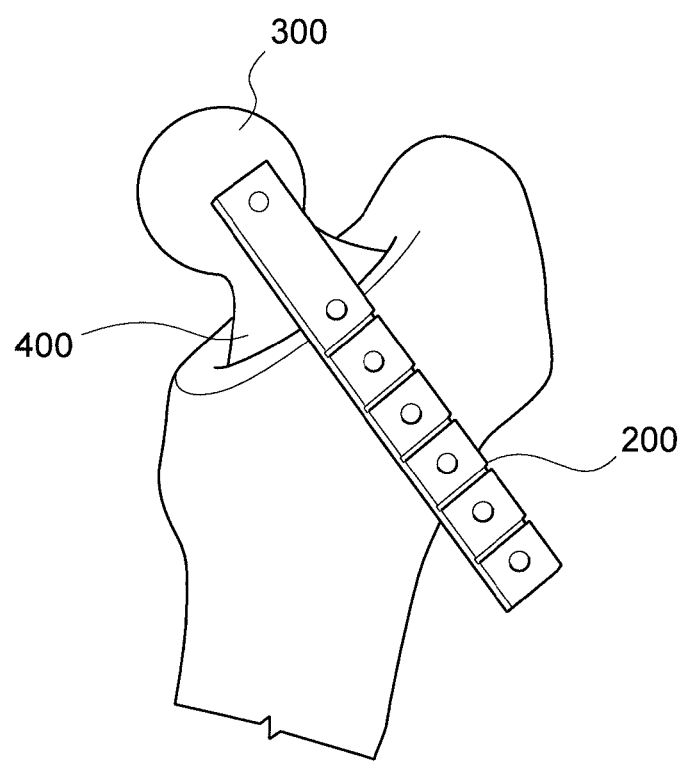
FIG. 11 shows the trochanter marking device connected to the trial femoral head.

As shown in FIG. 11, the connection element of the trochanter marking device 200 is inserted into the slot 310 on the trial femoral head component 300 at substantially 90°. This ensures that in the case of anti-version, the surgeon will be able to visualise a gap between the bone and the trochanter marking device.

Figure 12A:
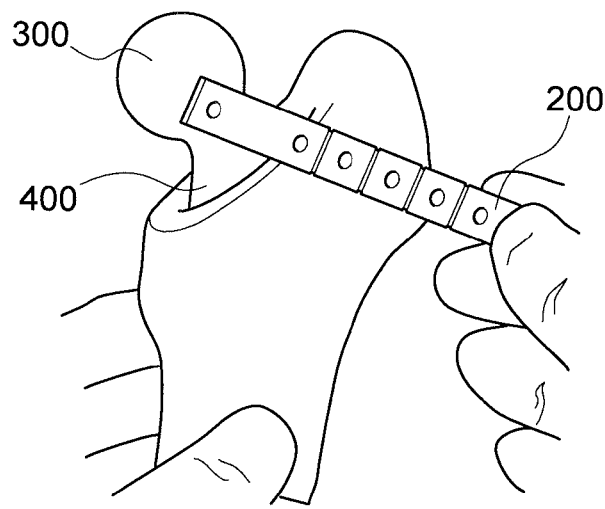
FIG. 12 shows the use of the trochanter marking device for assessing whether the centre of rotation of the trial femoral head is the same as the native femoral head.
Figure 12B:
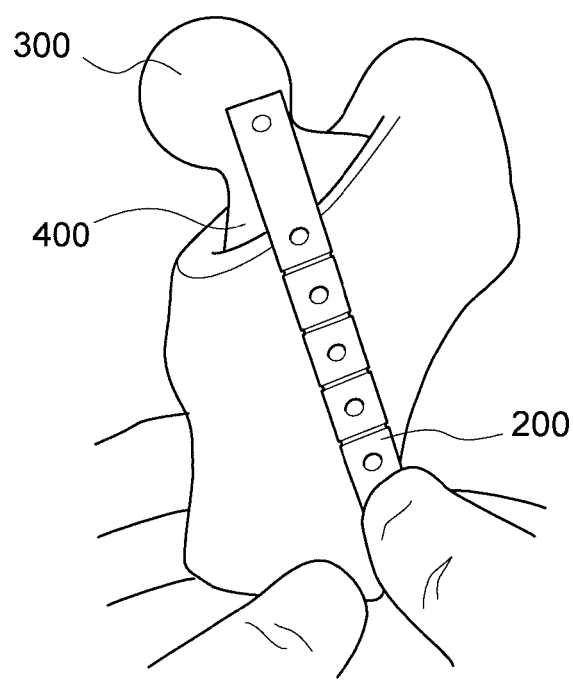

As shown in FIGS. 12a and 12b, the trochanter marking device 200 is pivoted to each of the first and second reference marks on the bone. If the aperture 214 (through which the bone marking tool made the reference marks) overlies both the reference marks, then the surgeon knows that the femoral head centre of rotation of the trial femoral head component is in the same position as the femoral head centre of rotation of the native femoral head. The centre of rotation has been successfully restored and, by extension, when the final implant (corresponding to the trial femoral head component) is implanted, leg length will remain unchanged.

Although particular constructions of the invention have been described, it will be appreciated that many modifications/additions and/or substitutions may be made within the scope of the claimed invention.

We claim:

1. A femoral head centre of rotation locating device comprising:
    an adjustable frame having a frame axis, the frame comprising:
    a central frame portion;
    a first jaw that is linearly moveable relative to the central frame portion along the frame axis and having a first femoral head contacting surface;
    a second jaw that is linearly moveable relative to the central frame portion along the frame axis and having a second femoral head contacting surface, and
    a gearwheel mounted on the central frame portion, the gear wheel having a centric aperture located substantially equidistant from the first and second femoral head contacting surfaces, the gear wheel being operably connected to each of the first and second moveable jaws by gear teeth provided on a surface of each of the first and second moveable jaws,
    wherein linear movement of the first jaw in a first direction rotates the gear wheel to cause reciprocal linear movement of the second jaw to maintain the centric aperture at a position equidistant from the first and second femoral head contacting surfaces to align the centric aperture with the native head centre of the femur as the first and second femoral head contacting surfaces come into contact with opposite surfaces of the femoral head;
    wherein each of the first and second jaw includes an end wall and a pair of arms extending therefrom, such that the end wall and pair of arms create a U-shape, with the pair of arms being parallel to one another.

2. The device according to claim 1, in which the gear teeth are provided at least partially along an inner surface of one of the arms of the first jaw and one of the arms of the second jaw.

3. The device according to claim 1, in which the first femoral head contacting surface and the second femoral head contacting surface comprises a projection extending from the end wall.

4. The device according to claim 3, in which the projection comprises a pair of spaced posts.

5. The device according to claim 4, further comprising a bone marking element, and in which the centric aperture of the gear wheel is dimensioned to receive the bone marking element for marking the position of the femoral head centre of rotation onto the femoral head.

6. The device according to claim 5, in which the bone marking element includes a first end configured to pierce the femoral head and second end configured to be impacted.

7. A kit for use in comparing the position of a femoral head centre of rotation of a native femoral head and a trial femoral head component, the kit comprising:
 (a) a femoral head centre of rotation locating device comprising:
  an adjustable frame having a frame axis, the frame comprising:
  a central frame portion;
  a first jaw that is linearly moveable relative to the central frame portion along the frame axis and having a first femoral head contacting surface;
  a second jaw that is linearly moveable relative to the central frame portion along the frame axis and having a second femoral head contacting surface, and a gearwheel mounted on the central frame portion, the gear wheel having a centric aperture located substantially equidistant from the first and second femoral head contacting surfaces, the gear wheel being operably connected to each of the first and second moveable jaws by gear teeth provided on a surface of each of the first and second moveable jaws,
  wherein linear movement of the first jaw in a first direction rotates the gear wheel to cause reciprocal linear movement of the second jaw to maintain the centric aperture at a position equidistant from the first and second femoral head contacting surfaces to align the centric aperture with the native head centre of the femur as the first and second femoral head contacting surfaces come into contact with opposite surfaces of the femoral head wherein each of the first and second jaw includes an end wall and a pair of arms extending therefrom, such that the end wall and pair of arms create a U-shape, with the pair of arms being parallel to one another;
 (b) a trochanter marking device comprising:
  a connection element configured for connecting the trochanter marking device to (i) the femoral head centre of rotation of the native femoral head and (ii) a femoral head centre of centre of rotation of a trial femoral head component, such that the trochanter marking device can pivot about each femoral head centre of rotation, and
  a marking aperture dimensioned for receiving a marking tool for marking the position of the marking aperture on the trochanter.

8. The kit of claim 7, in which the trochanter marking device includes a plurality of sections, each section including at least one marking aperture, and in which adjacent sections are connected via a frangible connection thereby enabling the trochanter marking device to be shortened by removal of a section.

9. The kit of claim 7, in which the femoral head centre of rotation locating device and/or the trochanter marking device is made of a plastic.

10. The kit of claim 7, in which the femoral head centre of rotation locating device and/or the trochanter marking device is disposable.

* * * * *